United States Patent [19]

Briner

[11] Patent Number: 5,124,486
[45] Date of Patent: Jun. 23, 1992

[54] PROCESS FOR THE PREPARATION OF CYCLIC KETONES

[75] Inventor: Paul H. Briner, Canterbury, England

[73] Assignee: Shell Research Limited, United Kingdom

[21] Appl. No.: 687,506

[22] Filed: Apr. 19, 1991

[30] Foreign Application Priority Data

May 1, 1990 [GB] United Kingdom ............... 9009776

[51] Int. Cl.$^5$ .............................................. C07C 45/74
[52] U.S. Cl. ........................................ 568/345; 568/393
[58] Field of Search ....................... 568/345, 407, 393

[56] References Cited

U.S. PATENT DOCUMENTS

| | | | |
|---|---|---|---|
| 2,194,704 | 3/1940 | Kroeger | 568/407 |
| 3,962,148 | 6/1976 | Hochstetler et al. | 568/345 |
| 4,169,859 | 10/1979 | Clough | 568/407 |
| 4,266,066 | 5/1981 | Spielmann et al. | 568/407 |

FOREIGN PATENT DOCUMENTS

| | | | |
|---|---|---|---|
| 3636057 | 1/1988 | Fed. Rep. of Germany | 568/345 |
| 58-35141 | 3/1983 | Japan | 568/345 |

OTHER PUBLICATIONS

Fukuzawa et al., J. Chem. Soc., Perk Trans 1, pp. 1473–1477 (1987).

Primary Examiner—James H. Reamer

[57] ABSTRACT

The invention provides a process for the preparation of cyclic ketones of the general formula

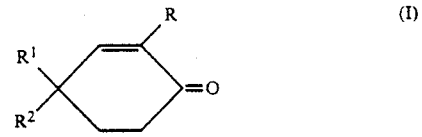

in which R represents an optionally substituted alkyl or cycloalkyl group and $R^1$ and $R^2$ independently represent an optionally substituted alkyl, cycloalkyl or aryl group, which comprises heating a compound of the general formula

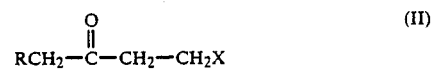

in which X represents a chlorine or bromine atom and R is as defined above, with a compound of the general formula

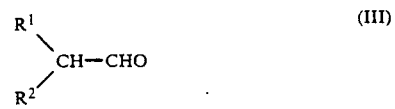

in which $R^1$ and $R^2$ are as defined above, in the presence of an organic acid.

Certain cyclic ketones of formula (I) are useful as intermediates in the preparation of certain fungicidally active cyclopentane derivatives.

6 Claims, No Drawings

PROCESS FOR THE PREPARATION OF CYCLIC KETONES

This invention relates to a process for the preparation of certain cyclic ketones, certain of which are useful as intermediates in the preparation of certain fungicidally active cyclopentane derivatives.

Org. Synth., 53, (1973), p. 48 et seq describes two methods for the preparation of 4,4-dimethyl-cyclohex-2-en-1-one. The first method consists of a base-promoted annelation reaction utilising methyl vinyl ketone and 2-methylpropanal (isobutyraldehyde). However, the yields obtained under these conditions are not particularly good and numerous byproducts are generated. A thorough study of this base-catalyzed condensation and the byproducts produced has been reported in J. Org. Chem., 44, No 23, (1979), pp. 4050–4055. The second method involves converting 2-methylpropanal to an enamine, such as 1-(2-methylpropenyl)pyrrolidine, condensing the enamine with methyl vinyl ketone, hydrolysing the resulting Diels-Alder adduct and finally cyclising under acidic conditions. Better yields are obtained by this method than the first method but the second method is somewhat lengthy and complicated. J. Org. Chem., 45, (1980), pp. 5399–5400 describes a third method for the preparation of 4,4-dimethylcyclohex-2-en-1-one and certain other unsaturated cyclic ketones by condensing methyl vinyl ketone with 2-methylpropanal (or certain other aldehydes) under acidic conditions. However, in addition to the problems already stated, all these methods require the use of methyl vinyl ketone which is toxic and unstable and therefore difficult to handle. Moreover, vinyl ketones as a class generally exhibit properties of toxicity and instability.

It has now been found that certain cyclic ketones can be prepared in good yield via a process which does not require the use of methyl vinyl ketone.

According to the present invention there is therefore provided a process for the preparation of a compound of the general formula

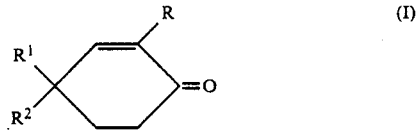

in which R represents an optionally substituted alkyl or cycloalkyl group and $R^1$ and $R^2$ independently represent an optionally substituted alkyl, cycloalkyl or aryl group, which comprises heating a compound of the general formula

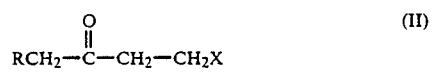

in which X represents a chlorine or bromine atom and R is as defined above, with a compound of the general formula

in which $R^1$ and $R^2$ are as defined above, in the presence of an organic acid.

When the compounds of formula I contain an alkyl substituent group, this may be linear or branched and may contain up to 12, preferably up to 6, and especially up to 4, carbon atoms. A cycloalkyl group may contain 3 to 8, especially 3 to 6, carbon atoms.

When any of the foregoing substituents are designated as being optionally substituted, the substituent groups which are optionally present may be any one or more of those customarily employed in the development of pesticidal compounds and/or the modification of such compounds to influence their structure/activity, persistence, penetration or other property. Specific examples of such substituents include, for example, halogen atoms, nitro, cyano, hydroxyl, cycloalkyl, alkayl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl and alkylamido groups. When any of the foregoing substituents represents or contains an alkyl substituent group, this may be linear or branched and may contain up to 12 preferably up to 6, and especially up to 4, carbon atoms.

It is preferred that R represents a $C_{1-6}$ alkyl or $C_{3-6}$ cycloalkyl group. More preferably, R represents a $C_{1-4}$ alkyl group.

It is also preferred that $R^1$ and $R^2$ independently represent a $C_{1-4}$ alkyl or $C_{3-6}$ cycloalkyl group. More preferably, $R^1$ and $R^2$ independently represent a $C_{1-4}$ alkyl group.

It is especially preferred that R represents a methyl, ethyl or propyl group, $R^1$ and $R^2$ both represent a methyl group and X represents a chlorine atom.

Preferably, the organic acid is an organic sulphonic acid such as methyl sulphonic acid or, especially, para-toluenesulphonic acid.

It is further preferred that the reaction is carried out in a solvent which has the ability to remove water azeotropically from the reaction mixture. Suitable solvents include aromatic solvents and chlorinated solvents, such as 1,2-dichloroethane.

The reaction is conveniently carried out at the reflux temperature of the solvent used.

It is also preferred that the compound of formula II is prepared by reacting ethene with a compound of the general formula

in which R and X are as previously defined, in a solvent in the presence of $AlX_3$ where X is as defined above.

The solvent is preferably a chlorinated solvent, such as 1,2-dichloroethane, and it is particularly preferred that the solvent is the same as that to be used in the subsequent reaction of the compound of formula II thus obtained with a compound of formula III.

Conveniently, the reaction is carried out at a temperature in the range from 0° to 30° C., preferably 5° to 25° C.

Most preferably, the compound of formula II is prepared in situ. Preferably, it is then used in the reaction with a compound of formula III without further purification.

Of the cyclic ketones that may be prepared by the process of the invention, 4,4-dimethylcyclohex-2-en-1-one is useful as an intermediate in the preparation of certain fungicidally active cyclopentane derivatives which form the subject of co-pending patent application EP-A2-0267778. Some of the intermediate compounds and process steps in the process used to synthesise compounds of EP-A2-0267778 from 4,4-dimethylcyclohex-2-en-1-one are the subject of copending European patent application no. EP-A1-0359305 and copending British patent applications nos. 8820607.3, 9019195.8, 9019192.5, 9019194.1, 9019193.3, 9019191.7 and 9019190.9.

The invention is further illustrated by the following Examples.

EXAMPLE 1

Preparation of 4,4-dimethylcyclohex-2-en-1-one
($R=H$, $R^1=R^2=CH_3$)

Ethanoyl chloride (78.5 g, 1 mole) was added over a period of 30 minutes to a suspension of aluminium chloride (140 g, 1.05 moles) in 1,2-dichloroethane (390 ml) whilst maintaining the temperature below 20° C. by cooling. Ethene (35 g, 1.25 moles) was then passed into the solution at 5°–10° C. over a period of 2 hours and the subsequent mixture worked up by slowly pouring into 2M hydrochloric acid (900 ml). The organic phase was separated and 2-methylpropanal (50.4 g, 0.7 moles) and para-toluenesulphonic acid (0.4 g, 21 mmoles) were added. The mixture was then refluxed with azeotropic water removal until no more water separated. The organic phase was then washed with 10% (w/v) sodium hydroxide (250 ml) by stirring at 60° C. for 15 minutes to destroy any traces of 4-chlorobutan-2-one and the solvent flashed. Fractionation gave 70 g 4,4-dimethylcyclohex-2-en-1-one, b.pt. 70°–72° C. at 20 mm Hg. (Yield: 80%)

NMR: (in CDCl$_3$ solvent, tetramethylsilane as reference). Characteristic peaks at: δ(ppm): 1.6 (6H, sinqlet), 1.92 (2H, triplet, J 7 Hz), 2.40 (2H, triplet, J7 Hz), 5.76 (1H, doublet, J10 Hz), 6.58 (1H, doublet, J10 Hz).

EXAMPLE 2

Preparation of 2,4,4-trimethylcyclohex-2-en-1-one
($R=R^1=R^2=CH_3$)

Aluminium chloride (60.6 g, 0.454 moles) Was added to 1,2-dichloroethane (200 ml) and the mixture cooled to about 0° C. Propanoyl chloride (40 g, 0.432 moles) was then added over a period of 20 minutes and the temperature of the reaction mixture allowed to rise to -20° C. to give a clear pale orange solution. This solution was stirred for 30 minutes and ethene (12 g, 0.432 moles) was then bubbled into the solution over a period of about 1½ hours. The mixture was then quenched in a mixture of concentrated hydrochloric acid (65 ml) and ice (330 ml) and the organic phase separated and back-washed with water (2×50 ml). 2-Methylpropanal (22 g, 0.3 moles) and para-toluenesulphonic acid (1.65 g, 8.64 mmoles) were then added and the mixture refluxed with azeotropic water removal until no more water separated. The organic phase was then washed with 10% (w/v) sodium hydroxide (200 ml) and the solvent removed. Distillation gave 30 g 2,4,4-trimethylcyclohex-2-en-1-one, b.pt. 40° C. at 0.3 mm Hg. (Yield: 72%)

EXAMPLE 3

Preparation of 2-ethyl-4,4-dimethylcyclohex-2-en-1-one
($R=C_2H_5$, $R^1=R^2=CH_3$)

Using 1-chlorohexan-3-one (20 g, 0.148 moles), 2-methylpropanal (10.8 g, 0.148 moles), para-toluenesulphonic acid (0.6 g, 3.0 mmoles) and 1,2-dichloroethane (100 ml), 6 g 2-ethyl-4,4-dimethylcyclohex-2-en-1-one, b.pt. 55° C. at 0.4 mm Hg, (Yield: 27%) were prepared by a method entirely analoqous to those described in Examples 1 and 2.

I claim:
1. A process for the preparation of a compound of the formula:

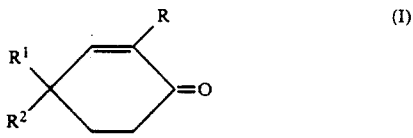

in which R represents an optionally substituted alkyl or cycloalkyl group and $R^1$ and $R^2$ independently represent an optionally substituted alkyl, cycloalkyl, or aryl group, said optional substituents being selected from the group consisting of halogen, nitro, cyano. hydroxyl, cycloalkyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl and alkylamido, which process comprises heating a compound of the formula:

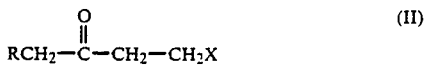

in which X represents a chlorine or bromine atom and R is as defined above, in the presence of a compound of the formula:

in which $R^1$ and $R^2$ are as defined above, and in the presence of an acid selected from the group consisting of methyl sulphonic acid or para-toluenesulphonic acid.

2. A process according to claim 1, wherein R is selected from the group consisting of $C_{1-6}$ alkyl and $C_{3-6}$ cycloalkyl.

3. A process according to claim 1, wherein $R^1$ and $R^2$ are independently selected from the group consisting of $C_{1-4}$ alkyl and $C_{3-6}$ cycloalkyl.

4. A process according to claim 1, wherein R is methyl, ethyl or propyl, $R^1$ and $R^2$ are each methyl, and X is chlorine.

5. A process according to claim 1, wherein the compound of formula (II) is prepared by reacting ethene with a compound of the formula:

in which R is as defined in claim 1 and X is chlorine or bromine, in a solvent in the presence of AlX$_3$, wherein X is chlorine or bromine.

6. A process according to claim 1, wherein the compound of formula II is formed in situ.

* * * * *